United States Patent [19]

Crawford et al.

[11] Patent Number: 5,003,814
[45] Date of Patent: Apr. 2, 1991

[54] SAMPLING PROCESSES FOR USE IN THE CONTROLLED ADDITION OF CONDITIONING MATERIAL TO SUSPENSIONS, SLUDGES AND THE LIKE AND APPARATUS THEREOF

[75] Inventors: Paul M. Crawford, Burlington; Herbert W. Campbell, Dundas; Michael J. Myers, Kilbride; Steven L. Siverns, Hamilton, all of Canada

[73] Assignee: Lenon Envionmental Inc., Ontario, Canada

[21] Appl. No.: 345,256

[22] Filed: May 1, 1989

Related U.S. Application Data

[63] Continuation-in-part of Ser. No. 187,801, Apr. 29, 1988, abandoned.

[51] Int. Cl.$^5$ .................................... G01M 11/10
[52] U.S. Cl. .................................... 73/59; 137/92
[58] Field of Search ............ 93/54, 59, 60, 862.22, 93/862.33; 137/92, 4; 210/709, 739, 96.1

[56] References Cited

U.S. PATENT DOCUMENTS

| | | | |
|---|---|---|---|
| 2,354,923 | 8/1944 | McNamee | 73/59 |
| 2,938,378 | 5/1960 | Canada et al. | 73/862.33 |
| 3,163,172 | 12/1964 | Buzzard | 73/54 |
| 3,292,422 | 12/1966 | Banks | 73/59 |
| 3,389,596 | 6/1968 | Lion et al. | 73/60 |
| 3,835,045 | 9/1974 | Hussissian | 210/709 |
| 3,938,890 | 2/1976 | Flavell | 73/862.33 |
| 4,077,252 | 3/1978 | Stutz et al. | 73/59 |
| 4,544,489 | 10/1985 | Campbell et al. | 210/709 |
| 4,685,328 | 8/1987 | Huebner et al. | 73/55 |

FOREIGN PATENT DOCUMENTS

481857 12/1953 Italy ..................................... 73/59

*Primary Examiner*—Hezron E. Williams

[57] ABSTRACT

The invention provides a sampling process and apparatus therefor for the control of the addition of expensive conditioning material, referred to as polymers, to suspensions, sludges and the like, particularly sewage sludge, to facilitate its dewatering. The process employs a viscometer able to measure rapidly the shear stress of the sludge and obtain a typical peak value characteristic of optimum conditioning of the sludge. The process and apparatus also operate in a new mode involving charging a sample vessel with unconditioned sludge, taking a measurement to obtain an "unconditioned" signal, and then filling with conditioned sludge and obtaining a "conditioned" signal, the unconditioned signal indicating the solids content of the sludge and being used to modify the signal controlling the polymer flow and therefore the dosage to compensate for this charge. The viscometer rotor and the vessel interior are rinsed to remove the conditioned sludge before a fresh batch of unconditioned sludge is introduced. The system employs a minimum-seeking algorithm to minimize polymer usage. Changes are made to the polymer flow rate when the conditioned signal change is greater than a dead-band straddling the optimum value, the minimum-seeking also taking place within the dead-band. It is sometimes found that the peak value/polymer flow rate characteristic includes a secondary peak, whereby the peak value reduces with increase of polymer flow, and this potentially unstable condition is detected and corrected.

26 Claims, 8 Drawing Sheets

SAMPLING PROCESSES FOR USE IN THE CONTROLLED ADDITION OF CONDITIONING MATERIAL TO SUSPENSIONS, SLUDGES AND THE LIKE AND APPARATUS THEREOF

CROSS-REFERENCE TO RELATED APPLICATION

This application is a continuation-in-part of our prior application Ser. No. 07/187,801, filed 04/29/88, now abandoned.

FIELD OF THE INVENTION

The present invention is concerned with improvements in or relating to sampling processes for use in the controlled addition of conditioning material to suspensions, sludges and the like, and to sampling apparatus therefor.

REVIEW OF THE PRIOR ART

There are a large number of commercial processes which involve the production and/or handling of suspensions, sludges and the like. One important example is waste water treatment which often generates two end products, namely a treated liquid effluent and a solid residue, the latter normally being present as a dilute suspension of relatively low solids content (e.g. 1-7% by weight), referred to in the industry as "sewage sludge". This sludge suspension requires further treatment and cannot normally be discarded in this form. Consequently in large treatment plants the sludge invariably is concentrated or dewatered before further processing is undertaken. Other examples are suspensions of coal fines, which may have solids contents of up to 30% by weight, suspensions of pulp and paper fibers and food waste suspensions or sludges; numerous other types of sludges and suspensions will be known in different industries and to those skilled in this particular art. Owing to the nature of these sludges and suspensions, particularly biological sludges, the dewatering rates are very slow unless they are pre-conditioned with chemicals to flocculate the solids. Current practice entails widespread use of organic polyelectrolytes (referred to herein as polymers) for this purpose Such polymers are quite effective but they represent a significant operation and maintenance cost. For example, the polymer costs for a sewage treatment plant intended to service an urban population of approximately 2 million (City of Montreal, Quebec, Canada) were for 1984 approximately $7 million dollars Canadian. Optimization of the polymer usage is therefore desirable as possibly generating substantial cost savings.

The fundamental characteristics of the sludges and suspensions and the associated water-binding mechanisms are poorly understood and hitherto the addition of the polymer has usually been made on the basis of a gross parameter, such as the total solids content, and usually is not adjusted during the day to take account of changes in either the incoming sludge concentration or any of its other characteristics. It is important for the operator not to let the sludge or suspension become under-conditioned, since this will deleteriously effect the dewatering and the quality of the resulting cake, and it is more usual to over-condition, resulting in wastage of the expensive conditioning polymers. It is therefore important from performance considerations as well as from cost to optimize the rate of addition of the conditioner to the sludge.

There is disclosed and claimed in U.S. Pat. No. 4,544,489, issued 1st Oct., 1985, inventors H. W. Campbell et al, the disclosure of which is incorporated herein by this reference, new processes and apparatus for the control of the addition of conditioning polymers to sludge, resulting from the discovery that, upon rheological examination of a sludge using a viscometer of controllable shear rate, it is found to exhibit a non-Newtonian plastic or pseudo-plastic flow, and possesses a characteristic initial yield stress, complicated however by the fact that most sludges are also thixotropic, possessing an internal structure which breaks down as a function of time and shear rate.

Tests carried out on sludge samples with different dosages of polymers, using an increasing shear rate, showed that an under-conditioned sludge exhibited a relatively smoothly increasing shear stress characteristic with increasing shear rate, from zero up to a rate at which turbulence occurred and resulted in a suddenly increased slope of the curve. As the polymer dosage increased it was eventually found that curves were obtained in which, at the lower end of the shear rate scale, the shear stress increased very rapidly at first, and then suddenly reversed and decreased over a subsequent period, so that the curve exhibited a characteristic peak; thereafter the shear stress again increased progressively with a suddenly increasing slope as turbulence began. Further increases in polymer dosage progressively increased the peak value but without affecting its general positioning on the curve. It was found that the appearance of this characteristic peak, with the slope of the curve passing through zero, corresponded closely to an optimum polymer dosage. It was postulated that the increasing shear stress observed corresponded to increasing flocculation of the solids, with the peak corresponding to optimum flocculation and subsequent breakdown of the flocculated material with increasing shear rate.

This therefore provided new processes, claimed in the said patent, for controlling the addition of dewatering conditioning material to a sewage sludge comprising the steps of measuring with a viscometer the value of its shear stress of the mixture to determine the existence or not of a predetermined maximum value; in the absence of detection of such a maximum value increasing the rate of addition of conditioning material; upon the detection of such a maximum value measuring the rate of subsequent decrease of the shear stress immediately following the maximum value; and increasing or decreasing or maintaining the rate of addition of the conditioning material respectively as the rate of decrease is less than, or more than, or about equal to a predetermined rate of said subsequent decrease.

It also resulted in new apparatus for the controlled addition of dewatering conditioning material to a sewage sludge including controllable pump means for supplying a flow of conditioning material to a flow of sewage sludge so that they mix to produce a sludge/material mixture; a viscometer; means operative to examine the viscometer output signals and control means responsive to such examination to control the controllable pump means in accordance with the process.

The apparatus specifically disclosed in that prior patent employs a separate sampling vessel into which is charged a sample of the mixture of sludge and conditioning material taken from the mainstream. Under the control of a computer the viscometer measures the shear stress of the sample in the vessel. The viscometer employed may be of the rotational type that measures the shear stress at an increasing rate of rotation, or alternatively that measures the shear stress at a constant speed of rotation over a period of time.

DEFINITION OF THE INVENTION

It is the principal object of the present invention to provide new sampling processes permitting improved control of the addition of the conditioning material to suspensions, sludges, and the like, and to provide new apparatus therefor.

In accordance with the present invention there is provided a sampling process for the controlled addition of dewatering conditioning material to suspensions or sludges to produce an optimized mixture thereof, comprising the steps of:

measuring with a viscometer in a quantity of suspension or sludge without added conditioning material the value of the shear stress thereof to obtain a corresponding unconditioned signal representative of the solids content of the suspension or sludge;

measuring with the viscometer in a quantity of the same suspension or sludge with added conditioning material the value of the shear stress of the mixture to obtain a corresponding conditioned signal;

controlling the rate of addition of the conditioning material to the suspension or sludge in accordance with the conditioned signal to obtain an optimum mixture of sludge or suspension and dewatering conditioning material; and utilizing the unconditioned signal to modify the conditioned signal to compensate for change in solids content of the suspension or sludge requiring a change in the rate of addition.

The unconditioned signal may be a low signal indicating a solids content of too low a value for satisfactory operation, resulting in an indication signal to that effect.

Alternatively, the unconditioned signal may be a high signal indicating a solids content of too high a value for satisfactory operation resulting in an indication signal to that effect.

The unconditioned signal may be used to modify the conditioned signal in accordance with the relations:

$$\text{New Control Signal} = \text{Old Control Signal} * (1 + \text{Change}) \quad (1)$$

where the "Change" is given by:

$$\text{Change} = \frac{(TP' - CP)}{TP'} * \text{GAIN} \quad (2)$$

and $$TP' = \frac{UCB}{TB} * TP*SG*OPSp + (100 - SG)*TP \quad (3)$$

where
"TP'" is the Adjusted Tune Peak value;
"UCB" is the Unconditioned Baseline value;
"TB" is the Tuned Base value;
"TP" is the Tuned Peak value;
"SG" is the Solids Gain factor;
"OPSp" is the Operator Setpoint;
"CP" is the Conditioned Peak Value; and
"GAIN" is the overall Gain factor for the equation.

The invention also embodies apparatus operating in accordance with the sampling process, the apparatus comprising a sampling vessel;

a viscometer having a rotatable rotor protruding into the vessel interior to be immersed in the suspension or sludge therein and adapted to produce a signal representative of the rheology of the suspension or sludge;

pipe and valve means connected to the vessel for charging the vessel interior in sequence with (a) unconditioned suspension or sludge;

(b) the same suspension or sludge with added conditioning material; and (c) water for rinsing the vessel interior;

means for operating the viscometer with the vessel filled with conditioned and unconditioned suspension or sludge to produce corresponding signals representative of the rheology of the suspension or sludge, and means for controlling the rate of addition of the conditioning material to the suspension or sludge responsive to the value of the measured unconditioned and conditioned signals.

The viscometer may comprise means for operating the rotor at a substantially constant speed for a predetermined period of time, and for measuring the torque applied to the rotor during that period of time.

Also in accordance with the invention there is provided a particular viscometer structure for use in the processes of the invention.

DESCRIPTION OF THE DRAWINGS

Particular preferred embodiments of the invention will now be described, by way of example, with reference to the accompanying diagrammatic drawings, wherein.

DESCRIPTION OF THE PREFERRED EMBODIMENTS

Figure 1:
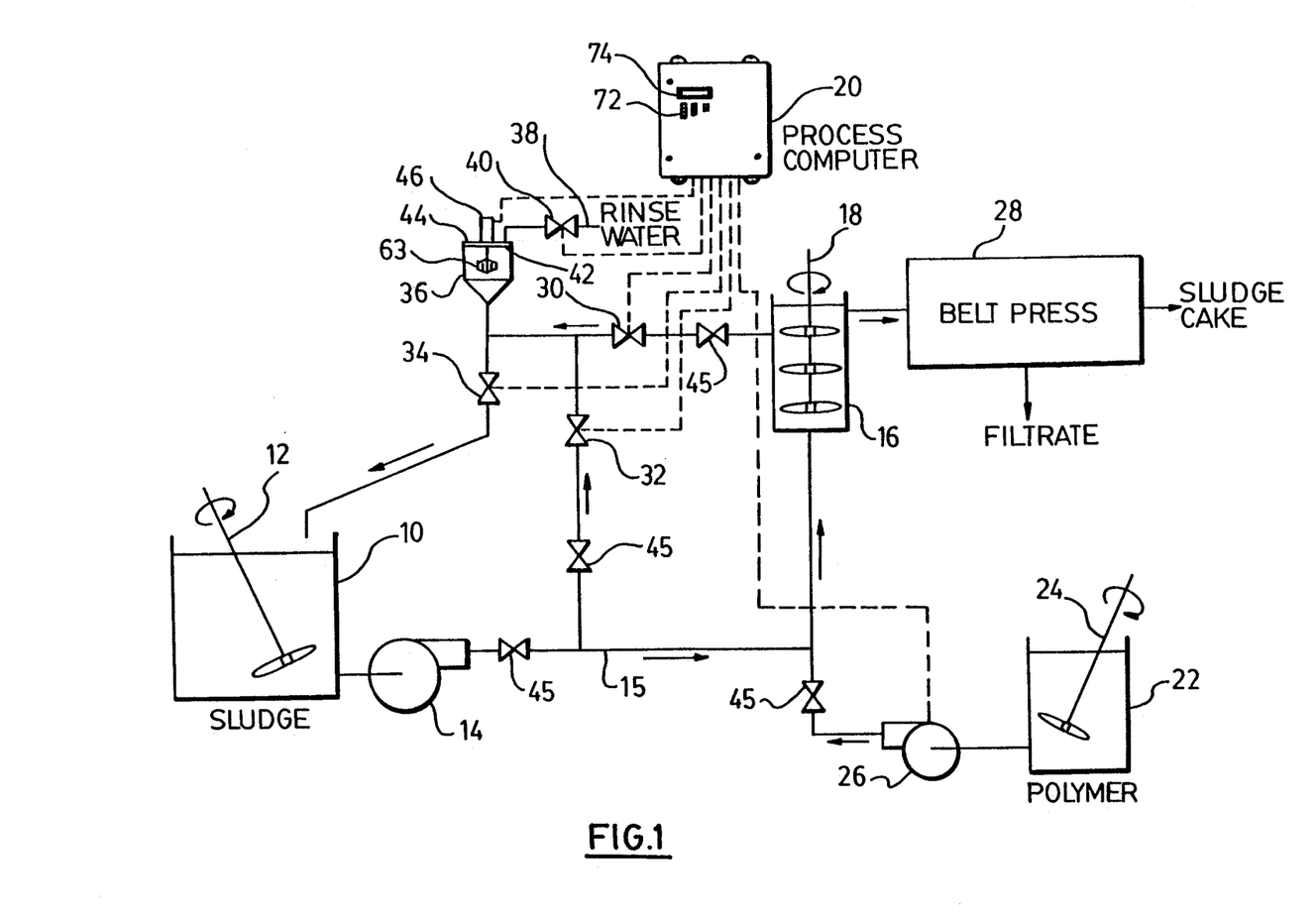
FIG. 1 is a general schematic representation of a sludge dewatering system in which the addition of polymer conditioning material is controlled employing the sampling processes and apparatus of the invention.

Referring now to FIG. 1, bulk sludge is usually delivered to a tank 10 and kept in suspended state by a stirrer 12, the contents of the tank being fed by a sludge pump 14 through a feed pipe 15 to a flocculator tank 16 provided with a manually controlled stirrer 18. For convenience in the following description reference is made only to sewage sludge and belt presses, but the application of the process and apparatus to other sludges and to suspensions, etc., as well as to other mechanical dewatering devices, will be apparent to those skilled in the art. Electrical connections to and from a process computer 20 by which the apparatus is controlled are shown by broken lines to distinguish them from the liquid feed pipes, which are shown by solid lines. It will be understood by those skilled in the art that the computer does not operate apparatus such as the pumps, valves, and stirrers directly, but through appropriate relays and switches. It is standard practice in the industry to add the polymer in the form of a solution or suspension thereof, which therefore is contained in a tank 22 provided with a stirrer 24. The liquid is fed from tank 22 by a controllable variable rate polymer feed pump 26 under the control of the process computer into the feed pipe 15 just ahead of its entry to the flocculator tank 16, in which thorough mixing of the sludge and polymer takes place assisted by the action of the stirrer 18. The mixed material is then fed to a belt press 28 which separates liquid from the sludge to result in the production of separate sludge cake and filtrate.

As and when a sample operation is required a computer controlled unconditioned sludge delivery valve 32 is opened for a predetermined period of time by computer 20, while valves 30 and 34 are closed, resulting in the delivery of a predetermined quantity of the unconditioned sludge directly from the feed pipe 15 to a sample vessel 36 in which the shear measurement takes place. Alternatively, if conditioned sludge delivery valve 30 is opened while valves 32 and 34 are closed conditioned sludge is delivered to the sample vessel 36. With valves 30 and 32 closed and drain valve 34 open the contents of the vessel 36 drain back into the sludge feed tank 10 or, because of the relatively small volume, can be discarded with the filtrate.

Again under control of the computer 20, as and when required, rinse water is delivered from rinse water feed pipe 38 through control valve 40 to three spray heads 42 (FIG. 1; only one indicated) mounted on lid 44 to protrude inside the vessel, so that all of the vessel interior and all of the viscometer measurement rotor therein can be sprayed with the rinse water, the thorough cleansing of the viscometer rotor being particularly important to maintain accuracy of the measurements. Manual valves 45 are provided for use as required, e.g. to isolate each section of the piping during cleaning and maintenance.

Figure 2:
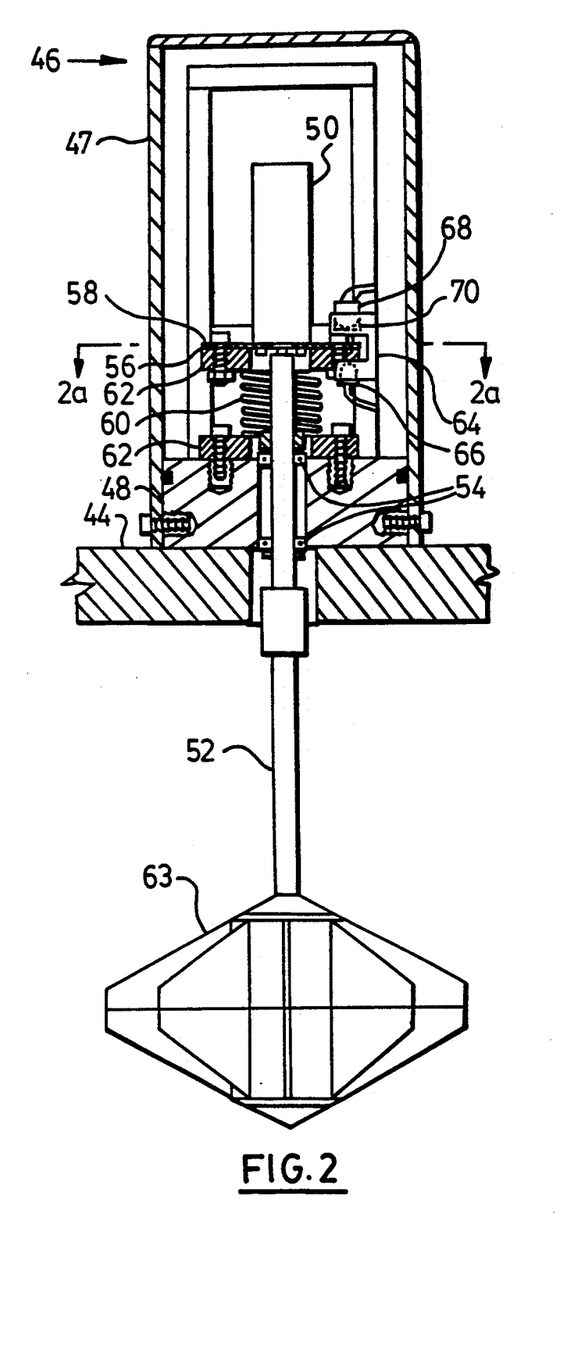
FIG. 2 is a part longitudinal cross-section and part side elevation to a larger scale of a viscometer used in the apparatus of FIG. 1.
Figure 2A:
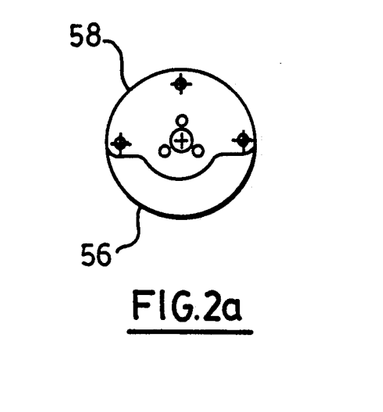
FIG. 2a is a plane section on the line 2a-2a in FIG. 2.

Referring now in addition to FIGS. 2 and 2a, the sample vessel 36 together with a sensor head 46 mounted on the lid 44 constitute a viscometer for measuring the shear stress of the sludge, this particular viscometer carrying out this measurement at a constant speed of rotation of its measurement rotor over a period of time. The head is enclosed in a housing 47 surrounding a base 48 by which the head is mounted on the lid 44. A D.C. motor 50 has its shaft 52 mounted in vertically spaced bearings 54 in the base 48, so that its axis of rotation is vertical. A thin circular disc 56 of polarizing material is mounted on a support 58, which is in turn fastened to the casing of the motor 50 so as to be rotatable therewith relative to the motor rotor and the shaft 52. The motor casing is not fixed against rotation and consequently will counter-rotate in reaction to the torque on the shaft 52, rotating the disc 56 with it. This reaction rotation is opposed by a coil spring 60 having its ends embedded in collars 62 which are fastened respectively to the fixed base 48 and the movable motor casing. If the motor is now operated to rotate its rotor and the shaft at a constant speed the angle of the counter-rotation of the motor casing will be proportional to the shear stress applied to the measurement rotor 63 by the sludge sample; the power of the motor 50 and the strength of the spring 50 are correlated so that the maximum value of this angle is just less than about 60 degrees.

The sheet 56 and its support 58 pass between the arms of a U-shaped detector mounting 64, in the lower arm of which is mounted a light-emitting diode 66, while the upper arm carries a light intensity detector 68 and a piece of polarizing material 70 interposed between the detector and the sheet 56, and thus also between the detector and the diode 66. The arrangement and mounting of the two polarizing elements is such that when the motor is stationary and its casing is in its rest position, their planes of polarization are aligned to give light transmission such that the signal from the detector 68 is about 15% of the maximum possible, so as to be on a suitably sensitive portion of the characteristic. As the shear stress of the sludge increases, and the counter-rotation of the motor casing increases correspondingly, the angle between the polarization planes increases, increasing the light transmission and the output signal. With such an arrangement an output signal can be obtained that is substantially linear over the range zero to sixty degrees, corresponding to about 80% of the available torque.

Referring again also to FIGS. 1, 2 and 2A the operation of the apparatus from start-up necessitates the setting by hand of a number of parameters employing an access key pad 72 at the process computer, and display 74 to show the parameter that is under adjustment. The rate of polymer flow from the pump 26 will initially be set by hand to a value known by the operator from historical data and visual observation of the dewatering performance to be approximately suitable for this sludge pump, belt press, etc.. The viscometer rotor 63 is rotated in air for a short period of time, e.g. about ten seconds, to ensure that it is working properly and not fouled with debris; an error message is given if a problem is detected. The valve 32 is opened to deliver unconditioned sludge to the vessel 36; an error signal is provided if the vessel does not fill within a preselected time period. The motor 50 is then operated to rotate the viscometer rotor for a period of about ten seconds at a suitable speed, e.g. about 30–60 r.p.m., usually about 40 r.p.m., the output signal of the detector 68 being observed and recorded and representing the rheological properties of the unconditioned sample. Three typical plots of torque measured with time for sludges of solids contents 2%, 3% and 4% respectively are shown in FIG. 3 and are labelled "unconditioned sludge baselines".

Figure 3:
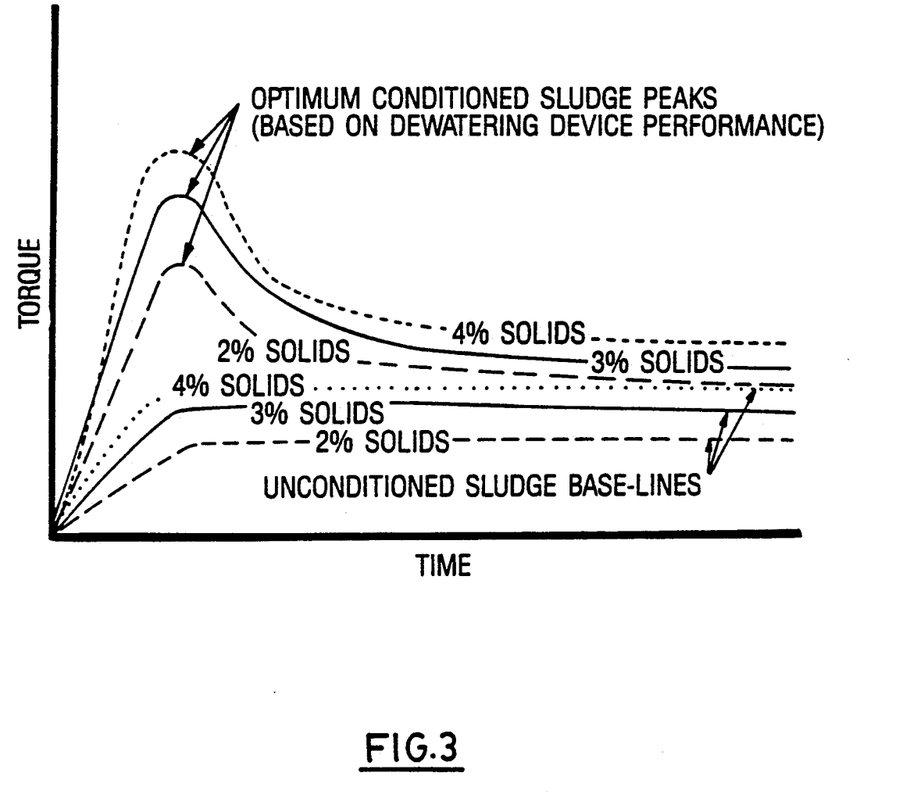
FIG. 3 is a graph of torque as measured by the viscometer with time, showing typical characteristics for conditioned and unconditioned materials of different solids contents.

FIG. 3 also shows typical plots obtained for three well-conditioned sludges of the same solids contents and it will be seen that they rise rapidly to a respective characteristic peak as the sludge resists the rotation of the viscometer rotor. Thereafter, as the rotor begins to shear the sludge the signal value decays from the peak, following a characteristic negative-going curve, and finally becoming almost constant at a conditioned sludge baseline value after the shearing action is complete. For the unconditioned sludges the respective signal peaks may not be seen at all, or if seen are so small as to be virtually non-existent, with the signals rising progressively from zero to almost constant baseline values, the log of which is proportional to the solids concentration of the respective sample. The values obtained for both the conditioned and unconditioned samples increase with increase in the solids contents and this characteristic is employed as described below in producing a control signal for control of the rate of polymer flow. The highly peaked values obtained with the conditioned sludge also increase with the solids content, and if the sludge is over-conditioned the peak on the torque/time plot will usually be higher and more pronounced, except for a special condition that is sometimes encountered, as described in more detail below.

It is found in practice that there is considerable variation in operating characteristics from plant to plant, depending for example on the composition of the sludge, the solids content of the sludge, the quantity of sludge to be handled per unit time, and the type of dewatering apparatus employed, added to which is the possibility of variation with time in an individual plant. The operator is able to enter an initial polymer flow rate signal value based on historical experience, as described above, and the system is then operated automatically to run a preselected number of tests (typically about five) on both unconditioned and conditioned sludges at this initial constant polymer flow rate, the data from these tests being averaged to produce a "tuned" unconditioned baseline value and a "tuned" conditioned peak value. These tuned values are then employed by the process controller for the automatic operation of the process. If at any time the operator suspects that the tuned values are no longer valid a fresh series of tests can be run to provide a new set.

The solids content of the sewage sludges encountered have been found to vary widely, e.g. within the range 1–5% and in one commercial system examined the concentration ranged from 1.2% to 4% with a median value of 2.5%, with the concentration below 2% for 20% of the period. It is in practice difficult to distinguish between a conditioned value caused by low solids content and one caused by insufficient polymer addition. This ambiguity is resolved in a system according to the invention, and the available sensitivity of the apparatus is readily increased down to solids contents as low as 0.3%, by the rheological measurement carried out by the apparatus on the unconditioned sludge immediately prior to the measurement carried out on what is effectively the corresponding conditioned sludge. Thus the conditioned measurement is carried out on sludge that passed earlier into the tank 16, but the time interval involved is sufficiently short for there not to be too great a change (if any) in solids content, which is moreover averaged to some extent by the mixing that takes place in the tank 16. The unconditioned value is representative of the relative solids concentration for the sample, and can therefore be used as a correction factor in the calculation that follows the measurement with the conditioned sludge. By application of the invention the sensor is able to produce a signal whose characteristic over time correlates well with the polymer dosage, and the polymer flow rate can be increased or decreased as required to obtain the response corresponding to optimum dosage.

Figure 4A:
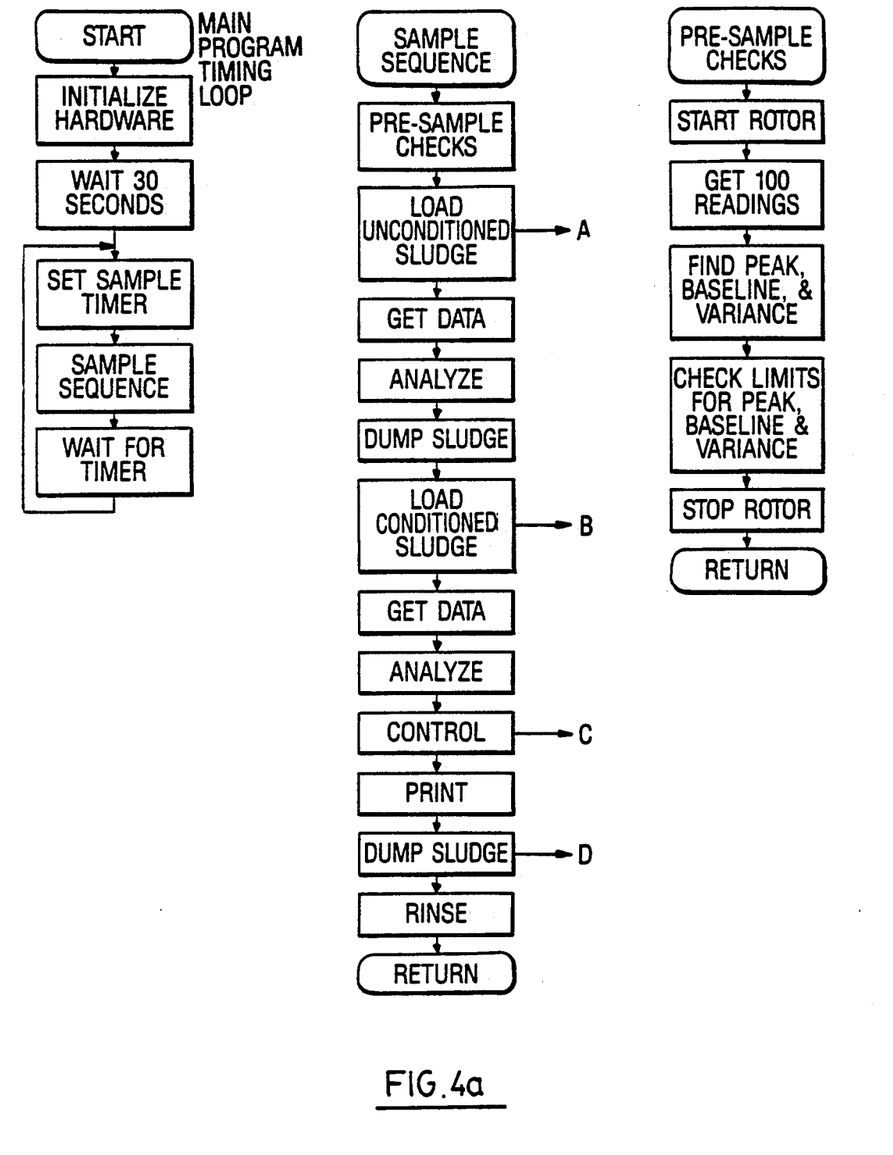
FIGS. 4a, 4b and 4c together constitute a flow chart of a typical process of the invention.
Figure 4B:
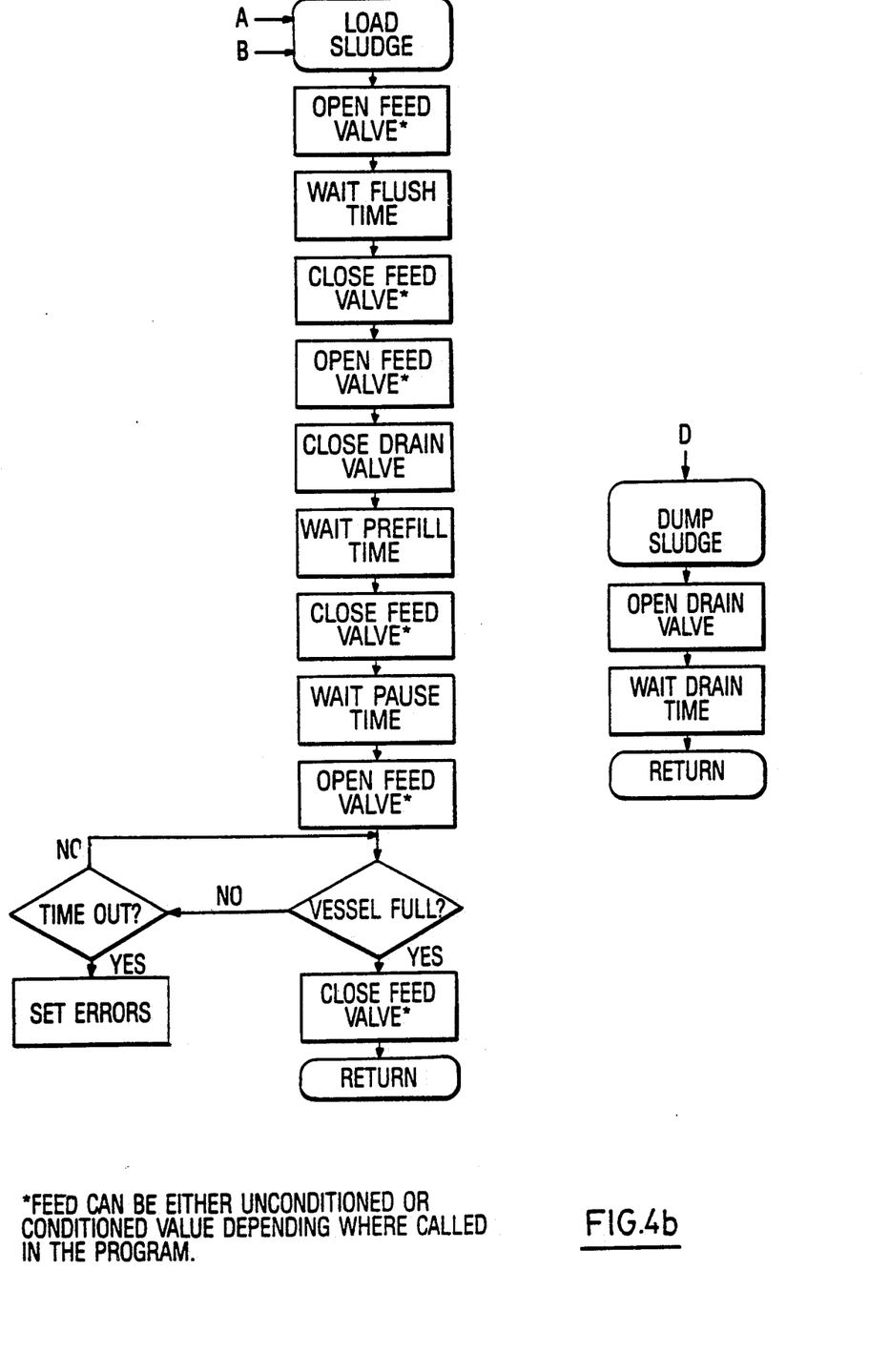
Figure 4C:
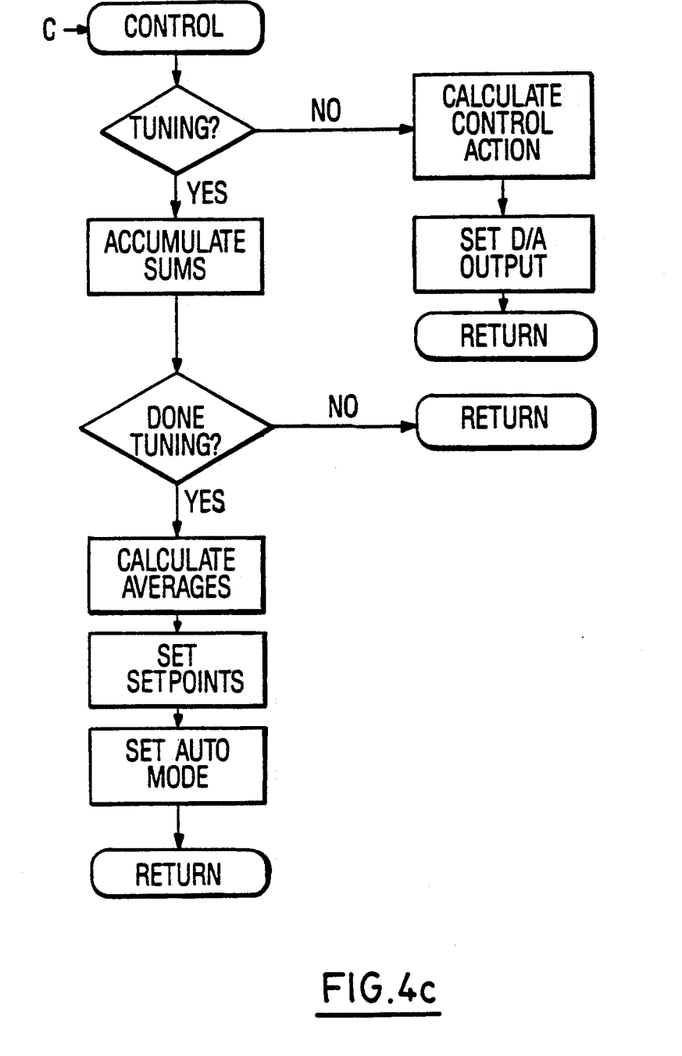

FIGS. 4a, 4b and 4c together constitute a flow chart showing in greater detail the steps of the process involved and the operation of the apparatus.

The initial signal obtained with unconditioned sludge is employed for a number of important additional purposes. For some sludges if the solids content is too low it may not be possible to produce a conditioned peak at all, despite the addition of large quantities of polymer, and there is then the possibility that the system attempts to correct for the "problem" by increasing the dosage, when instead the system should be shut down and the operator warned. This initial signal can be used for this purpose. At the other extreme the solids content may be so high that the viscometer motor is not powerful enough to reach the peak value in the available time, or cannot even rotate the viscometer rotor at a suitable speed; once again the signal obtained can be used to provide a warning to the operator that correction is required, usually involving replacement of the viscometer rotor with one of smaller size, so that it is easier to rotate and a useful signal can be obtained. At all times the unconditioned signal obtained constitutes a zero-conditioned baseline that can be used as described below by comparison with the tuned base value obtained during the tuning procedure, and to ensure that the sludge is within the predetermined parameters.

The unconditioned sludge is then discharged and valve 30 operated to fill the vessel with conditioned sludge, the corresponding measurement is taken to obtain a "conditioned" peak signal, and the vessel interior and the viscometer rotor rinsed for a preselected time period, usually about 30 seconds. This conditioned peak signal is then utilized with the "unconditioned" signal and a new "control" signal is derived from the conditioned peak signal using the following relations:

$$\text{New Control Signal} = \text{Old Control Signal} * (1 + \text{Change}) \quad (1)$$

where the "Change" is given by:

$$\text{Change} = \frac{(TP' - CP)}{TP'} * \text{GAIN} \quad (2)$$

and $$TP' = \frac{UCB}{TB} * TP * SG * OPSp + (100 - SG) * TP \quad (3)$$

where
"TP'" is the Adjusted Tune Peak value;
"UCB" is the Unconditioned Baseline value;
"TB" is the Tuned Base value;
"TP" is the Tuned Peak value;
"SG" is the Solids Gain factor;
"OPSp" is the Operator Setpoint;
"CP" is the Conditioned Peak Value; and
"GAIN" is the overall Gain factor for the equation.

This new or final control signal is employed to determine the rate of feed by the polymer pump 26, and it may be noted that the equation does not include, and does not need to include, measurement of the sludge flow rate. This sample sequence is then repeated at suitable intervals set by the operator. Owing to the time taken for each sample cycle a repetition period of three minutes or less means that the apparatus samples continuously; a suitable practical upper limit for this parameter is about 30 minutes.

Figure 5:
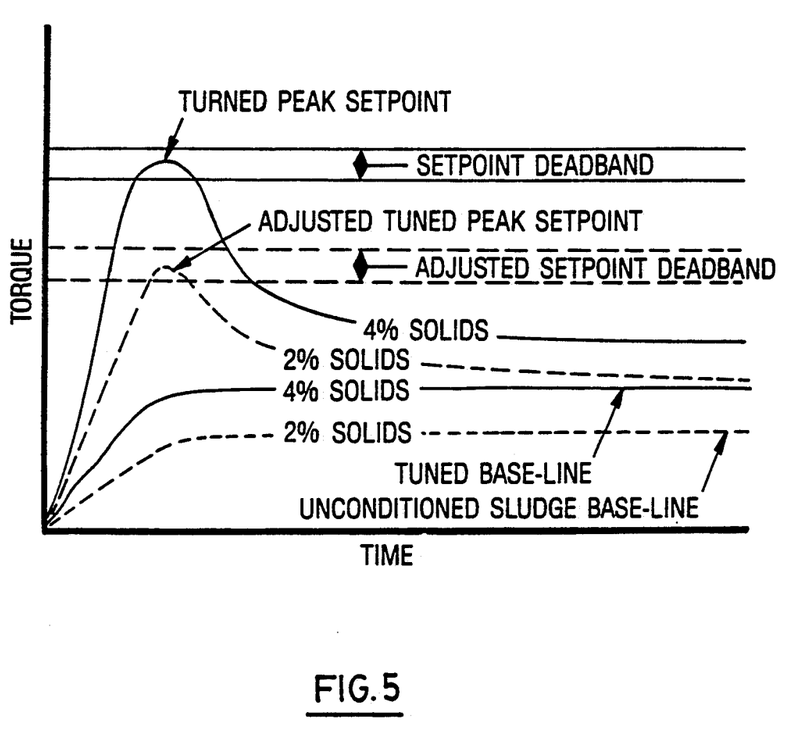
FIG. 5 is a graph similar to FIG. 3 to illustrate a control feature of the process.

Referring now to FIG. 5, the control system operates with the tuned values in order to develop an optimized control signal, as described above. The control program employs a minimum-seeking algorithm whereby even if all of the conditions for optimum operation are met the system will still always attempt to decrease the polymer flow rate by a small preselected amount. Therefore with relatively "steady state" conditions of sludge flow and solids content the system will cycle the polymer flow rate above and below the minimum value which meets the set point requirements. If upon measuring the unconditioned base-line value it corresponds to the tuned base-line value then the system will employ the corresponding tuned peak value for comparison with the newly measured peak value, while if there is a change in unconditioned base-line value the system will adjust the peak value for comparison in accordance with this change.

Thus, in operating this particular embodiment in accordance with the relations (1)-(3) above the viscometer will take a measurement with a new sample of unconditioned sludge and obtain a new unconditioned base-line signal value. This new baseline signal value will be compared with the stored tuned base-line value and if it differs from the tuned value the corresponding tuned peak value will be multiplied by the ratio of new base-line value/tuned base-line value to obtain an adjusted tuned peak value. The newly measured conditioned peak value then obtained by the operation of the viscometer with the corresponding sample of conditioned sludge is then compared with the adjusted tuned value and the rate of polymer flow increased or decreased accordingly.

FIG. 5 illustrates the situation where there has been a decrease in solids content of the sludge from 4% to 2%, with corresponding changes in the tuned peak setpoint and tuned base-line to a new adjusted tuned peak setpoint and a new unconditioned sludge base-line respectively. Because of minor variability in the sampling process it is not desirable to compare a newly measured conditioned sludge peak value directly with the memory stored adjusted tuned peak setpoint, and instead the system provides an adjustable "dead-band" range of values straddling this value (typically ±5% thereof). If the newly measured value is within the dead-band range then the decision made is to reduce the polymer flow rate in accordance with the minimum-seeking requirement, and the decision to increase polymer flow rate is only made when the measured value is below the lowest dead-band value. If the newly measured value is above the maximum dead-band value then the flow rate would be decreased by an amount greater than the usual "minimum-seeking" amount. Since the dead-band range is proportional to the peak value it is also adjusted in value corresponding to the peak setpoint that it straddles.

Figure 6:
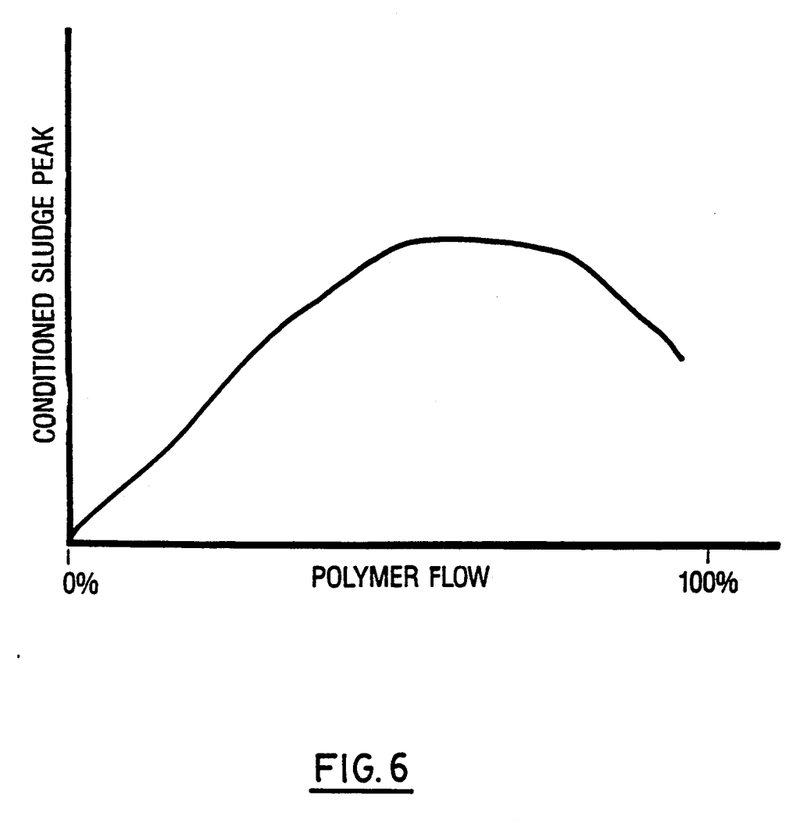
FIG. 6 is a graph showing the effect found in some processes upon the value of the conditioned sludge peak with increasing value of the rate of flow of the conditioning polymer.

FIG. 6 illustrates an unexpected relation that has sometimes been found between the value of the conditioned sludge peak and the rate of polymer flow, this flow rate as shown in the Figure being an arbitrary value dependent upon the parameters of the system under control, and in which the value of 100% is set principally by the maximum pumping capacity of the polymer pump 26, it being assumed for simplicity of description that the solids content is constant and that therefore the unconditioned sludge base-line value is constant. It has been found that, contrary to expectation, the response in conditioned peak value to increasing proportion of polymer is not always a monotonically increasing curve, with increases in polymer addition resulting in increases in peak value, with perhaps the attainment of a maximum value after which there is little or no increase. Instead quite frequently this monotonic relation does not hold, and with some sludges the conditioned peak value (called the primary peak value to distinguish it) when plotted against polymer flow rate may reach a secondary peak value, and thereafter decrease with increasing polymer addition. At the present time we have no explanation for this effect. If this secondary peak condition is present an unstable situation exists in that with primary peak values on the positive-going side of the characteristic the system will continue to increase the polymer flow rate; if the secondary peak value is overshot and the negative-going side of the characteristic is reached the reduction in primary peak value will signal to the system to increase polymer flow, leading to a further reduction in primary peak value, this situation continuing until the polymer pump is operating at 100% capacity. Although the system will continue to seek a minimum polymer flow rate by reduction thereof under the control of the algorithm, this minimum-seeking will be defeated and reversed once the lower dead-band value is passed. In some systems the situation may not be reached because the maximum flow capacity of the polymer pump is not sufficient for the secondary peak value to be passed.

To avoid this possibility the system monitors separately the correspondence between the polymer flow rate and the primary conditioned peak values; more specifically the system examines the ratio of the differences in primary peak values to the differences in polymer flow rates for three successive readings (two differences resulting from three readings). If comparison of these two differences from these three successive readings show that the slope of the primary peak values characteristic has become negative, indicating that the secondary peak has been passed and the "downside" of the characteristic has been reached, then the system is reversed and the rate of polymer feed is decreased, despite the increase in primary peak value, until the secondary peak has been passed and an increase in polymer flow rate again produces an increase in the conditioned primary peak value; with the system again on the "upside" of the characteristic its operation is again reversed to revert to normal operation.

Thus, to illustrate the application to this specific embodiment let it be assumed that the solids content remains sufficiently constant for there not to be a change in the newly measured base-line values, so that there is no change in the tuned base-line values or the tuned peak setpoint; in practice of course the algorithm will also compensate for any such changes. The three successive newly measured conditioned peak values will be compared with the corresponding tuned (preset) peak setpoint values and three respective primary difference values will then be obtained; these three primary difference values will then be compared and if the resulting two secondary difference values show an increase with time and the polymer flow rate signal is also decreasing with time, then the secondary peak has been passed and the system is on the negative-going downside of the characteristic; the operation of the system is therefore reversed and the polymer flow rate decreased until the system is back on the positive-going upside of the characteristic, when it can revert to the more usual operation. It should be noted that in practice the control signal change is usually limited to an adjustable maximum value (usually ±5%) of the actual polymer flow signal to avoid too abrupt swings in its value.

The control algorithm employed ensures that the system does not respond too rapidly to relatively large changes in conditioning, but instead increases or decreases the flow rate in small increments which occur at a minimum interval of time (e.g. about 10 minutes) so that the system changes smoothly and progressively without overshoot, due perhaps to an aberrant inaccurate signal produced between accurate signals. It has been found by application of the system that savings of the relatively expensive polymer of as much as 24% can be obtained. In addition it is found that if belt presses are used they can be operated more efficiently with up to 20% increase in throughput, because of the reduced possibility of belt blinding, tracking problems, and the expensive downtime that results from these problems.

We claim:

1. A sampling process for the controlled addition of dewatering conditioning material to suspensions or sludges to produce an optimized mixture thereof, comprising the steps of:

measuring with a viscometer in a quantity of suspension or sludge without added conditioning material the value of the shear stress thereof to obtain a corresponding unconditioned signal representative of the solids content of the suspension or sludge;

measuring with the viscometer in a quantity of the same suspension or sludge with added conditioning material the value of the shear stress of the mixture to obtain a corresponding conditioned signal;

controlling the rate of addition of the conditioning material to the suspension or sludge in accordance with the conditioned signal to obtain an optimum mixture of sludge or suspension and dewatering conditioning material; and utilizing the unconditioned signal to modify the conditioned signal to compensate for change in solids content of the suspension or sludge requiring a change in the rate of addition.

2. A sampling process as claimed in claim 1, comprising:

obtaining with the viscometer a plurality of successive unconditioned base-line signals and obtaining therefrom a tuned unconditioned base-line signal;

obtaining with the viscometer a plurality of successive conditioned peak signals and obtaining therefrom a tuned conditioned peak signal;

measuring with the viscometer a new unconditioned base-line signal and comparing it with the tuned unconditioned base-line signal;

modifying the tuned conditioned peak signal in accordance with the result of the comparison of the new and tuned unconditioned base-line signals to obtain an adjusted tuned conditioned peak signal which has been adjusted for change in solid content of the sludge or suspension as indicated by a difference in values of the new and tuned unconditioned base-line signals;

measuring with the viscometer a new conditioned peak signal and comparing it with the adjusted tuned conditioned peak signal; and adjusting the rate of addition of the conditioning material to the suspension or sludge in response to a difference in the new and adjusted tuned conditioned peak signals.

3. A sampling process as claimed in claim 2, wherein the tuned conditioned base signal is modified to obtain an adjusted tuned conditioned peak signal in accordance with the ratio of the new unconditioned base-line signal to the tuned unconditioned base-line signal.

4. A sampling process as claimed in claim 1, wherein upon production of a low unconditioned signal indicating a solids content of too low value for satisfactory operation an indication signal to that effect is produced.

5. A sampling process as claimed in claim 1, wherein upon production of a high unconditioned signal indicating a solids content of too high a value for satisfactory operation an indication signal to that effect is produced.

6. A sampling process as claimed in claim 1, comprising the additional steps of:

producing a flow rate signal representative of the rate of flow of dewatering conditioning material;

upon production of conditioned signals with primary peak values comparing the primary peak values of successive conditioned signals with one another to determine whether the differences between successive primary peak values increase or decrease with increasing flow rate signal;

upon increase of the difference between the conditioned signal primary peak values with increase of flow rate signal, indicating that a secondary peak of the corresponding characteristic has been passed and a negative-going portion of the characteristic has been reached, reversing the operation of the system to decrease the flow rate until the secondary peak has been passed and decrease of flow rate produces an increase of difference between successive conditioned signal primary peak values, whereupon the original operation of the system is restored.

7. A sampling process as claimed in claim 1, comprising the additional steps of:

producing a flow rate signal representative of the rate of flow of dewatering conditioning material;

upon the production of conditioned signals with primary peak values comparing each primary peak value of successive conditioned signals with a corresponding preset value thereof to obtain a respective primary difference value;

comparing the three primary difference values obtained from the measurement of three successive primary peak value thereof to obtain a respective primary difference value;

upon increase of the secondary difference values with increase of flow rate, indicating that a secondary peak of the corresponding characteristic has been passed and a negative-going portion of the characteristic has been reached, reversing the operation of the system to decrease the flow rate until the secondary peak has been passed and decrease of flow rate produces and increase of the secondary difference values, whereupon the original operation of the system is restored.

8. A process as claimed in claim 1, wherein upon obtaining an optimum conditioned signal peak value corresponding to an optimum mixture the system is operative to reduce the rate of addition of dewatering conditioning material by a predetermined amount to seek the minimum rate of addition to produce the optimum conditioned signal peak value.

9. A sampling process as claimed in claim 1, wherein a newly measured conditioned signal value is compared with a previously measured tuned conditioned signal value within a dead-band range of values straddling the tuned value, and the rate of addition of the dewatering conditioning material is changed when the newly measured value is outside the dead-band range of values.

10. A sampling process as claimed in claim 1, wherein a newly measured conditioned signal value is compared with a previously measured tuned conditioned signal value within a dead-band range of values straddling the previously measured value, wherein upon obtaining a newly measured conditioned signal peak value within the dead-band range the system is operative to reduce the rate of addition of dewatering conditioning material by a predetermined amount to seek the minimum rate of addition to produce an optimum conditioned signal peak value, and wherein the rate of addition of the dewatering conditioning material is only changed except to seek the minimum rate of addition when the newly measured conditioned signal value is outside the dead-band range of values.

11. A sampling process as claimed in claim 1, wherein the unconditioned signal is used to modify the conditioned signal in accordance with the relations:

$$\text{New Control Signal} = \text{Old Control Signal} * (1+\text{Change}) \quad (1)$$

where the "Change" is given by:

$$\text{Change} = \frac{(TP' - CP)}{TP'} * \text{GAIN} \quad (2)$$

and $$TP' = \frac{UCB}{TB} * TP * SG * OPSp + (100 - SG) * TP \quad (3)$$

where
"TP'" is the Adjusted Tune Peak value;
"UCB" is the Unconditioned Baseline value;
"TB" is the Tuned Base value;
"TP" is the Tuned Peak value;
"SG" is the Solids Gain factor;
"OPSp" is the Operator Setpoint;
"CP" is the Conditioned Peak Value; and
"GAIN" is the overall Gain factor for the equation.

12. Apparatus for sampling suspensions or sludges and for control of the addition of dewatering conditioning material thereto to produce an optimized mixture, the apparatus comprising:
a sampling vessel;
a viscometer having a rotatable rotor protruding into the vessel interior to be immersed in a suspension or sludge therein and adapted to produce a signal representative of the rheology of the suspension or sludge;
pipe and valve means connected to the vessel for charging the vessel interior in a sequence with
(a) unconditioned suspension or sludge;
(b) the same suspension or sludge with added conditioning material; and
(c) water for rinsing the vessel interior;
valve control means connected to said valve means for operation thereof in the said sequence
viscometer operating means for operating the viscometer with the vessel filled with unconditioned and conditioned suspension or sludge to produce respective corresponding unconditioned and conditioned signals representative of the respective shear stress of the suspension or sludge, the unconditioned signal being representative of the solids content of the suspension or sludge;
signal utilizing means receiving the unconditioned and conditioned signals, producing a pump means control signal therefrom and utilizing the unconditioned signal to modify the conditioned signal so as to produce the pump means control signal compensated for change in solids content of the suspension or sludge requiring a change in the rate of addition of conditioning material; and
controllable pump means controlled by the pump means control signal to control the rate of addition of the conditioning material to the suspension or sludge so as to obtain an optimized mixture of sludge or suspension and dewatering conditioning material.

13. Apparatus as claimed in claim 12, wherein the signal utilizing means produces a pump means control signal responsive to the value of the measured conditioned signal as modified in accordance with change of the unconditioned signal from a set point value thereof corresponding to a change in the solids content of the suspension or sludge sufficient to require such modification of the measured conditioned signal.

14. Apparatus as claimed in claim 12, wherein the viscometer comprises means for operating the viscometer rotor at a substantially constant speed for a predetermined period of time, and for measuring the torque applied to the viscometer rotor during that period of time.

15. Apparatus as claimed in claim 12, wherein the viscometer comprises:
a motor having a casing, a motor rotor mounted therein, and a drive shaft rotatable with the motor rotor relative to the casing;
a viscometer rotor for insertion into the material whose rheology is to be determined mounted on the shaft and rotatable therewith;
means for applying electric power to the motor to produce relative rotation between the motor rotor and the casing;
spring means connected to the motor casing and opposing the counter rotation thereof resulting from the shearing of the material by the viscometer rotor; and
means for measuring the counter rotation of the motor casing in accordance with the counter-torque applied to the motor rotor by the material.

16. Apparatus as claimed in claim 15, wherein the means for measuring the said counter rotation of the motor casing comprises a first polarizing element rotatable with the motor casing, and a second stationary polarizing element, the planes of polarization of the two elements being rotatable relative to one another with rotation of the first element, the light transmission of the two elements thereby varying in accordance with their relative rotation;
a light source on one side of the two elements projecting light at the two elements for transmission therethrough; and
a light detector at the other side of the two elements receiving light transmitted through the two elements and producing a corresponding electric output signal.

17. Apparatus as claimed in claim 12, wherein the viscometer operating means operate the viscometer to obtain a plurality of successive unconditioned base-line signals representative of the respective shear stress of the suspension or sludge, and to obtain a plurality of successive conditioned peak signals;
wherein the signal utilizing means obtains from the said two pluralities of successive signals respectively a tuned unconditioned base-line and a tuned conditioned peak signal; wherein the viscometer operating means operates the viscometer to obtain a new unconditioned base-line signal;
wherein the signal utilizing means modifies the tuned conditioned peak signal in accordance with the result of the comparison of the new and tuned unconditioned base-line signals to obtain an adjusted tuned conditioned peak signal which has been adjusted for change in solids content of the sludge or suspension as indicated by a difference in values of the new and tuned unconditioned base-line signals;

wherein thereafter the viscometer operating means operates the viscometer to obtain a new conditioned peak signal; and wherein the signal utilizing means compares the new conditioned peak signal with the adjusted tuned conditioned peak signal and adjusts the pump means control signal to adjust the rate of addition of the conditioning material to the suspension or sludge in response to a difference in the new and adjusted tuned conditioned peak signals.

18. Apparatus as claimed in claim 17, wherein the signal utilizing means modifies the tuned conditioned peak signal to obtain an adjusted tuned conditioned peak signal in accordance with the ratio of the new unconditioned base-line signal to the tuned unconditioned base-line signal;

19. Apparatus as claimed in claim 12, and including annunciation means operated by the signal utilization means;

wherein upon production by the viscometer and supply to the signal utilizing means of a low unconditioned signal indicating a solids content of too low value for satisfactory operation the signal utilization means operates the annunciation means to produce an indication signal to that effect.

20. Apparatus as claimed in claim 12, and including annunciation means operated by the signal utilization means;

wherein upon production by the viscometer and supply to the signal utilizing means of a high unconditioned signal indicating a solids content of too high a value for satisfactory operation the signal utilization means operates the annunciation means to produce an indication signal to that effect.

21. Apparatus as claimed in claim 12, wherein the signal utilization means produces a flow rate signal representative of the rate of flow of dewatering conditioning material;

wherein the signal utilization means examines the conditioned signals for the production of conditioned signals with primary peak values and, upon the production of such signals, compares the primary peak values of successive conditioned signals with one another to determine whether the differences between successive primary peak values increase or decrease with increasing flow rate signal; and wherein upon increase of the difference between the conditioned signal primary peak values with increase of flow rate signal, indicating that a secondary peak of the corresponding characteristic has been passed and a negative-going portion of the characteristic has been reached, the signal utilization means reverse the operation of the system to decrease the flow rate until the secondary peak has been passed and decrease of flow rate produces an increase of difference between successive conditioned signal primary peak values, whereupon the signal utilization means restores the original operation of the system.

22. Apparatus as claimed in claim 12, wherein the signal utilization means produces a flow rate signal representative of the rate of flow of dewatering conditioning material;

wherein the signal utilization means examines the conditioned signals for the production of conditioned signals with primary peak values and, upon the production of such signals, compares each primary peak value of successive conditioned signals with a corresponding preset value thereof to obtain a respective primary difference value;

wherein the signal utilization means compares the three primary difference values obtained from the measurement of three successive primary peak values to obtain two secondary difference values; and wherein upon increase of the secondary difference values with increase of flow rate, indicating that a secondary peak of the corresponding characteristic has been passed and a negative-going portion of the characteristic has been reached, the signal utilization means reverses the operation of the system to decrease the flow rate until the secondary peak has been passed and decrease of flow rate produces an increase of the secondary difference values, whereupon the signal utilization means restores the operation of the system.

23. Apparatus as claimed in claim 12, wherein the signal utilization means is operative upon obtaining an optimum conditioned signal peak value corresponding to an optimum mixture of suspension or sludge and dewatering conditioning material to produce a pump means control signal which reduces the rate of addition of dewatering conditioning material by a predetermined amount to seek the minimum rate of addition to produce the optimum conditioned signal peak value.

24. Apparatus as claimed in claim 12, wherein the signal utilization means compares a newly measured conditioned signal value with a previously measured tuned conditioned signal value within a dead-band range of values straddling the tuned value, and the signal utilization means changes the pump means control signal to change the rate of addition of the dewatering conditioning material when the newly measured conditioned signal value is outside the dead-band range of values.

25. Apparatus as claimed in claim 12, wherein the signal utilization means compares a newly measured conditioned signal value with a previously measured tuned conditioned signal value within a dead-band range of values straddling the previously measured value, wherein upon obtaining a newly measured conditioned signal peak value within the dead-band range the signal utilization means is operative to produce a pump means control signal reducing the rate of addition of dewatering conditioning material by a predetermined amount to seek the minimum rate of addition to produce an optimum conditioned signal peak value, and wherein the signal utilization means is operative to change the rate of addition of the dewatering conditioning material, except to seek the minimum rate of addition, only when the newly measured conditioned signal value is outside the dead-band range of values.

26. Apparatus as claimed in claim 12, wherein the signal utilization means is operative to use the unconditioned signal to modify the conditioned signal in accordance with the relations:

New Control Signal = Old Control Signal * (1 + Change)     (1)

where the "Change" is given by:

$$\text{Change} = \frac{(TP' - CP)}{TP'} * \text{GAIN} \qquad (2)$$

and $$TP' = \frac{UCB}{TB} * TP*SG*OPSp + (100 - SG)*TP \qquad (3)$$

where

"TP'" is the Adjusted Tune Peak value;
"UCB" is the Unconditioned Baseline value;
"TB" is the Tuned Base value;
"TP" is the Tuned Peak value;
"SG" is the Solids Gain factor;
"OPSp" is the Operator Setpoint;
"CP" is the Conditioned Peak Value; and
"GAIN" is the overall Gain factor for the equation.

* * * * *

UNITED STATES PATENT OFFICE
CERTIFICATE OF CORRECTION

Patent No. 5,003,814   Dated April 2, 1991

Inventor(s) Paul M. CRAWFORD; Herbert W. CAMPBELL; Michael J. MYERS; and Steven L. SIVERNS It is certified that error appears in the above-identified patent and that said Letters Patent is hereby corrected as shown below:

On the title page, item [73] Assignee: should read as follows:
Assignee: Zenon Environmental Inc., Ontario, Canada Signed and Sealed this Twenty-eighth Day of July, 1992

Attest:

DOUGLAS B. COMER

Attesting Officer   Acting Commissioner of Patents and Trademarks